United States Patent [19]

Casutt et al.

[11] Patent Number: 4,739,071

[45] Date of Patent: Apr. 19, 1988

[54] PROCESS FOR THE PREPARATION OF ENANTIOMERS

[75] Inventors: Michael Casutt, Pfungstadt; Eike Poetsch, Mühltal, both of Fed. Rep. of Germany

[73] Assignee: Merck Patent Gesellschaft mit Beschrankter Haftung, Darmstadt, Fed. Rep. of Germany

[21] Appl. No.: 934,080

[22] Filed: Nov. 24, 1986

[30] Foreign Application Priority Data

Nov. 23, 1985 [DE] Fed. Rep. of Germany ....... 3541450

[51] Int. Cl.$^4$ ............................................ C07D 233/32
[52] U.S. Cl. ................................... 548/321; 560/124; 560/190; 562/401
[58] Field of Search ................. 548/321; 560/124, 190

[56] References Cited

PUBLICATIONS

Mikolajczyk, M., et al., *J. Am. Chem. Soc.*, 101(5), 1302–1303 (1979).
Chemical Abstracts, 94:4061j (1981) [Borgulya, J., et al., *Synthesis*, 1980, (7), 545–547].
Chemical Abstracts, 98:34938a (1983) [Rehwinkel et al., *Synthesis*, 1982, (10), 826–827].
Jacques, J., et al., *Enantiomers, Racemates, and Resolutions*, Wiley-Interscience, New York, 1981, pp. 253–259.

*Primary Examiner*—Richard A. Schwartz
*Attorney, Agent, or Firm*—Millen & White

[57] ABSTRACT

Enantiomers of optically active dicarboxylic acid monoesters are obtained by subjecting them to intramolecular rearrangement involving reversal of the direction of rotation.

22 Claims, No Drawings

PROCESS FOR THE PREPARATION OF ENANTIOMERS

BACKGROUND OF THE INVENTION

The invention relates to a process for the preparation of enantiomers of optically active dicarboxylic acid monoesters by intramolecular rearrangement.

Enantiomers of optically active dicarboxylic acid monoesters are valuable intermediate products in the preparation of optically active compounds, such as, for example (−)-pantolactone (Seebach, Wasmuth; Helv. Chim. Acta 63 (1980), 197) or the pheromone anthopleurin (Musich, Rapoport; J. Amer. Chem. Soc. 100 (1978), 4865).

A number of processes for the preparation of enantiomeric dicarboxylic acid monoesters are known. Thus, dicarboxylic acid diesters can be partially hydrolyzed by chemical means (for example Durham et al. in Org. Synth. Coll. Vol. IV, Wiley, New York, 1963, p. 635). Enzymatic processes of hydrolysis, as disclosed, for example, in EP-A 0,084,892 and JP-A 57,198,098, afford an enantiomer directly. Monoesters are also obtained from dicarboxylic anhydrides by alcoholysis (Houben-Weyl, Methoden der Organischen Chemie ("Methods of Organic Chemistry"), Georg-Thieme-Verlag, Stuttgart, Volumes VIII+E5). The dicarboxylic acid monoesters obtained by the above processes can be resolved into the optical antipodes by known methods for resolving racemates (for example in P. Newman: Optical Resolution Procedures for Chemical Compounds, Vol. 2, Optical Resolution Information Center, Manhattan College, Riverdale, N.Y., 1981), for example via the formation of diastereomeric salts, as described in EP-A 0,092,194 or DE-A 3,431,294.

These procedures known up to the present time exhibit a number of disadvantages. Thus, at the best only half of the total amount of desired enantiomer employed in the resolution process can be obtained from the racemic mixture of the enantiomeric dicarboxylic acid monoesters. The undesired enantiomeric which remains must be reconverted into a racemic form accessible to optical resolution. This can be effected, for example, by esterification to give the corresponding dicarboxylic acid diester, which can be partially hydrolyzed again. Furthermore, the undesired, optically active half-ester can be completely saponified to give the dicarboxylic acid, and the latter, after the conversion into the anhydride, can be converted again into a mixture of optically resolvable half-esters by means of an alcohol. The complete conversion of the undesired enantiomer into the desired enantiomer requires the processes of optical resolution and reconversion into a racemate form to be carried out, in some cases, several times.

There is therefore a need for a process which effects the conversion of optically active half-esters of dicarboxylic acid into one another without additional process stages and thus permits enantiomers of these half-esters to be prepared in a simple manner.

SUMMARY OF THE INVENTION

An object of this invention is to provide a process which facilitates conversion of enantiomers of dicarboxylic acid monoesters into one another.

Upon further study of the specification and appended claims, further objects and advantages of this invention will become apparent to those skilled in the art.

This object is achieved according to the invention by means of a process for the preparation of enantiomers of optically active dicarboxylic acid monoesters, involving the isolation of one enantiomer, characterized in that the monoester employed is subjected to an intramolecular rearrangement and the desired enantiomer is, if appropriate, removed. During the course of this process a reversal of the direction of rotation of the monoester employed is achieved.

The intramolecular rearrangement of carboxylic acids and esters of different carboxylic acids is known (cf. Houben-Weyl, loc. cit.). Equilibrium mixtures obtained in this reaction can often be influenced towards one product by removing one reactant.

Monoesters formed from achiral dicarboxylic acids and optically active alcohols undergo a racemization in the alcohol part under the conditions of acidolysis (Balfe et al., J. Chem. Soc. 1946, 803).

On the basis of the product to be expected in the case of an intramolecular rearrangement of the dicarboxylic acid monoesters which is optically active in the carboxylic acid part, it was therefore all the more surprising that the rearrangement of the monoesters takes place in a virtually uniform manner without appreciable formation of byproducts.

The conditions which are known for a transesterification reaction are particularly suitable for use in the process according to the invention. The transfer of the alcohol radical is catalyzed, for example, by H+ ions, ion exchangers, molecular sieves, Lewis acids, salts of alkali metals or subgroup metals or basic compounds, such as alkali or alkaline earth metal hydroxides or alcoholates or anion exchangers.

Catalysts which are particularly suitable are proton acids such as sulfuric acid, phosphoric acid, perchloric acid, methanesulfonic acid, toluenesulfonic acid or boric acid, Lewis acids, such as borontrifluoride, for example in the form of its diethyl ether adduct, and also alkali metal salts, such as sodium acetate, potassium cyanide or sodium cyanide, subgroup metal salts, such as triphenylphosphine-palladium(0) or triphenylphosphine-nickel(0) complexes, and also alkoxytrialkyltin compounds or titanium(V) alcoholates.

The reaction is carried out in a simple manner. The optically active monoesters, or enantiomeric mixtures thereof, of open-chain or cyclic 1, ω-dicarboxylic acids are employed as the enantiomers to be rearranged.

In the event that mirror planes are present in the formulae of the dicarboxylic acids on which the monoesters are based, pairs of enantiomers having the same quantitative direction of rotation for each of the antipodes are present and correspond to the general formulae I to III,

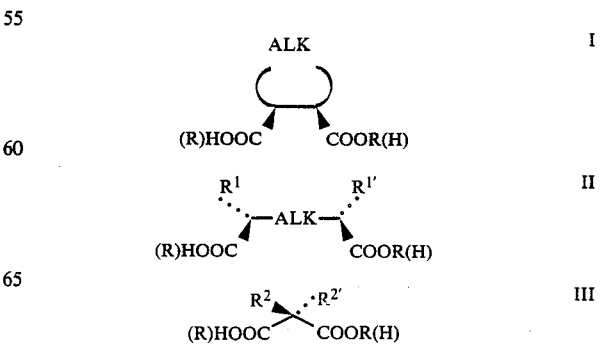

wherein

R—OH is an alcohol suitable for the formation of the monoesters,

ALK is a carbon chain which is unsubstituted or symmetrically substituted with respect to the carbonyl groups and $R^1$, $R^{1'}$, $R^2$, $R^{2'}$ are organic radicals other than hydrogen, subject to the proviso that $R^1$ and $R^{1'}$ are the same, but $R^2$ and $R^{2'}$ are different.

The precise nature of $R^1$, $R^{1'}$, $R^2$ and $R^{2'}$ and the substitution generally on the di-acids structures is not critical. Thus, aliphatic, aromatic, saturated, unsaturated, hydrocarbon, non-hydrocarbon (e.g. hetero), cyclic, acyclic, etc. moieties are included.

If the substituents $R^1$ and $R^{1'}$ in Formula II are different and if the substituent in the structural unit ALK is unsymmetrical with respect to the carbonyl groups, the diastereomer pairs then have quantitatively different values of optical rotation.

Thus, the dicarboxylic acid monoester being treated per this invention must have the same skeletal structure as its opposite monoester, i.e., as the monoester which is obtained by the transesterification of this invention.

Substitution in the structural unit ALK is to be understood as meaning also the replacement of one or more $CH_2$ groups by hetero-atoms, such as O, N, or S, by —CH=CH— or —C≡C— groups or by carbocyclic or heterocyclic rings.

For example, the dicarboxylic acid monoesters derived from any one of the fundamental structures of a to g emerge as sets of enantiomers and the enantiomers of each set can be converted into one another by the process according to the invention:

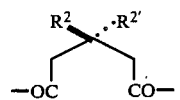
a

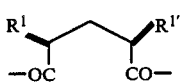
b

c

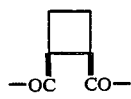
d

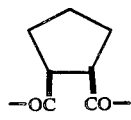
e

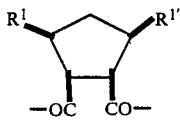
f

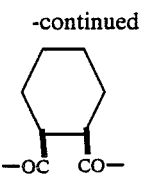
g

Dicarboxylic acid monoesters having a cyclic structure are particularly suitable for conversion by the process according to the invention, especially monoesters having three-, four-, five- and six-membered rings.

Within the context of the present invention the nature of the alcohols forming the half-esters is not critical. Either open-chain or cyclic alcohols can be employed. Selection is preferably made from the group comprising primary alcohols.

The rearrangement of the optically active dicarboxylic acid monoesters is preferably carried out in an inert organic solvent, and the degree of racemization proves to be independent of the solvent. The only factor affected by the nature of the solvent is the period of time required for equilibrium to be established. Solvents which are very suitable are, in particular, ethers, such as diethyl ether, di-n-butyl ether, tetrahydrofuran, dioxane or anisol, ketones, such as acetone, butanone or cyclohexanone, amides, such as dimethylformamide or phosphoric acid hexamethyltriamide, hydrocarbons, such as carbon tetrachloride or tetrachloroethylene, and sulphoxides, such as dimethyl sulphoxide or sulpholane. The rearrangement can also be carried out in the absence of a solvent, for example merely by heating the components in the presence of a suitable catalyst. The reaction temperature is usually about $-50°$ to $+250°$ C., preferably about $0°$ to $120°$ C. At these temperatures the rearrangement reactions are, as a rule, complete after about 15 minutes to 48 hours.

The rearrangement is preferably carried out by dissolving the dicarboxylic acid monoester, or the mixture of enantiomers thereof, to be racemized in a suitable solvent, adding the catalyst and heating the reaction mixture to the temperature required for the rearrangement, it being preferably to stir during the reaction period. The mixture is worked up after the reaction has been carried out preferably by removing the solvent and subjecting the residue to a resolution process suitable for optically active carboxylic acids (such as, for example, that indicated in P. Newman, ibid.).

It is preferable to convert the resulting racemate, by means of an optically active base, into a mixture of diastereomeric salts, which are separated, for example, by chromatography, extractive distribution or mechanical selection, but particularly by crystallization. The desired optically active dicarboxylic acid monoester is obtained from its diastereomeric salt, for example by liberation with acids, in particular by means of dilute mineral acids, from the salts which have been isolated.

In a preferred embodiment of the present invention, the crystallization of the desired enantiomer or one of its salts is carried out during the transesterification, and the monoester employed is thereby converted virtually completely into the desired enantiomer.

Thus, a salt, which is optically a single-substance, crystallizes out on cooling, for example, from solutions of diastereomeric salts which are saturated at the elevated temperature required for carrying out the rearrangement. After this single-substance salt has been removed, more of the diastereomeric salt of the enantiomer or enantiomer mixture to be rearranged is added to the reaction solution at an elevated temperature and, when the rearrangement has taken place, a further amount of the single-substance diastereomeric salt is isolated after cooling, a supersaturated solution being maintained. In a preferred multiple repetition of successive saturation, rearrangement and removal of the salt of one enantiomer, virtually the whole of the dicarboxylic acid monoester employed is converted into one enantiomer.

It is also known that single-substance enantiomers are capable, under certain conditions, of crystallizing directly from the corresponding racemate (see Collet et al., Chemical Reviews 80 (1980), 215). Dicarboxylic acid monoesters which are accessible to spontaneous separation can be converted into one another particularly advantageously by the process according to the invention. If there are suitable differences in solubility between the enantiomers and the racemate under the conditions used for the rearrangement, virtually complete conversion of the dicarboxylic acid monoester enantiomers into a single-substance enantiomer is possible in a single process stage.

The process according to the invention for the preparation of enantiomers is particularly suitable for the preparation of enantiomers of cis-1,3-dibenzyl-2-oxoimidazolidine-4,5-dicarboxylic acid monesters. Monoesters of this type are valuable intermediate products for the preparation of optically active lactones and thiolactones, as described, for example, in Gerecke et al., Helv. Chim. Acta 53 (1970), 991–999, and also for the preparation of optically active biotin, as described, for example, in German Pat. No. 2,058,234 and German Pat. No. 2,331,244.

The present invention thus provides a very advantageous process for the rearrangement, in a simple manner and in high yields, of enantiomeric dicarboxylic acid monoesters and which permits the preparation thereof in a high state of optical purity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

0.29 g (3 mmol) of orthophosphoric acid are added to 5.74 g (15 mmol) of (4R,5S)-cis-1,3-dibenzyl-5-ethoxycarbonyl-2-oxoimidazolidine-4-carboxylic acid in 60 ml of toluene, and the mixture is heated under reflux for 32 hours. After cooling to room temperature, the product is washed free from acid with water and is dried, concentrated and crystallized from ether/petroleum ether; yield: 4.95 g (86.2% of theory) of (4RS,5RS)-cis-1,3-dibenzyl-5-ethoxycarbonyl-2-oxoimidazoline-4-carboxylic acid; $[\alpha]_{365}^{20}=0.0°$ (c=1, DMF).

EXAMPLE 2

10 mol % of methanesulphonic acid are added to 5.74 g (15 mmol) of (4R,5S)-cis-1,3-dibenzyl-5-ethoxycarbonyl-2-oxoimidazoline-4-carboxylic acid in 60 ml of toluene, and the mixture is heated under reflux for 18 hours. After the product has been washed free from acid with water, 4.3 g (15 mmol) of (+)-dehydroabietylamine are added under hot conditions. When the mixture has cooled to room temperature, 3.5 g (70% of theory, relative to the enantiomer present) of (+)-dehydroabietylamine (4R,5S)-cis-1,3-dibenzyl-5-ethoxycarbonyl-2-oxoimidazoline-4-carboxylate; $[\alpha]_{365}^{20}=+48.2°$ (c=2, ethanol).

After concentration and crystallization, the mother liquor remaining after the removal of the above dehydroabietylamine salt affords 4 g (80% of theory, relative to the enantiomer present) of (+)-dehydroabietylamine (4S,5R)-cis-1,3-dibenzyl-5-ethoxycarbonyl-2-oxoimidazoline-4-carboxylate.

The free monoesters can be obtained from the dehydroabietylamine salts, for example by the process indicated in German Offenlegungsschrift No. 3,431,294.

EXAMPLE 3

5.74 g (15 mmol) of (4R,5S)-cis-1,3-dibenzyl-5-ethoxycarbonyl-2-oxoimidazoline-4-carboxylic acid are racemized as indicated in Example 1. When the product has been washed free from acid with water, 2.5 g (15 mmol) of (+)-ephedrine are added and the mixture is heated to 60° C. for a short time, with stirring, and is then allowed to stand at room temperature for 24 hours. The crystals are filtered off with suction and rinsed with a little toluene. Subsequent resolution of salts by known processes (for example German Patent Specification No. 2,058,248) gives 2.4 g (83.6% of theory) of (4S,5R)-cis-1,3-dibenzyl-5-ethoxycarbonyl-2-oxoimidazolidine-4-carboxylic acid; $[\alpha]_{365}^{20}=-21.8°$ (c=1, DMF).

2.7 g (94% of theory) of (4R,5S)-cis-1,3-dibenzyl-5-ethoxycarbonyl-2-oxoimidazoline-4-carboxylic acid are obtained from the mother liquor remaining after the removal of the (4S,5R)-monoester ephedrine salt; $[\alpha]_{365}^{20}=+22.1°$ (c=1; DMF).

EXAMPLE 4

8.2 g (20 mmol) of (4R,5S)-cis-1,3-dibenzyl-5-methoxy-ethoxycarbonyl-2-oximidazoline-4-carboxylic acid (obtainable from cis-1,3-dibenzylhexahydro-1H-furo[3,4-d]imidazole-2,4,6-trione and ethylene glycol monomethyl ether, the racemate being resolved by means of (+)-ephedrine; $[\alpha]_{365}^{20}-6.7\%$ (c=1, DMF)) are subjected to rearrangement by the procedure indicated in Example 2 in benzene and with the addition of methanesulphonic acid. 96% of theory of (4RS,5RS)-cis-1,3-dibenzyl-5-methoxy-ethoxycarbonyl-2-oxoimidazolidine-4-carboxylic acid are obtained; $[\alpha]_{365}^{20}=+0°$.

EXAMPLE 5

9.0 g (20 mmol) of (4R,5S)-cis-1,3-dibenzyl-5-benzyloxycarbonyl-2-oxoimidazoline-4-carboxylic acid (German Offenlegungsschrift No. 3,522,145) are subjected to rearrangement for 26 hours in toluene, using orthophosphoric acid, as indicated in Example 1; yield: 94.5% of theory.

EXAMPLE 6

9.0 g (20 mmol) of (4S,5R)-cis-1,3-dibenzyl-5-benzyloxycarbonyl-2-oxoimidazolidine-4-carboxylic acid (German Offenlegungsschrift No. 3,522,145) are subjected to rearrangement for 24 hours in toluene, using orthophosphoric acid, as indicated in Example 1; yield: 96% of theory.

EXAMPLE 7

8.6 g (50 mmol) of (1R,2S)-cis-3,3-dimethyl-2-methoxycarbonylcyclopropanecarboxylic acid ($[\alpha]_D^{20} = 17.5°$; obtained from the racemate by means of (+)-ephedrine are subjected to rearrangement for 18 hours in toluene in the presence of orthophosphoric acid, in accordance with Example 1. Yield: 72% of theory; $[\alpha]_D^{20} = 0.0°$ (c=1, chloroform).

EXAMPLE 8

17.4 g (0.1 mol) of monoethyl (−)-ethylmethylmalonate (Kenyon, Ross, J. Chem. Soc. 1951, 3407; $[\alpha]_D^{25} - 3.5°$ (c=5, chloroform)) are subjected to rearrangement in benzene and with the addition of methanesulphonic acid by the procedure indicated in Example 2. The resulting product has $[\alpha]_D^{25} = 0.0°$ (c=6, chloroform).

EXAMPLE 9

2 g (5.1 mmol) of (4R,5S)-cis-1,3-dibenzyl-5-allyloxycarbonyl-2-oxoimidazolidine-4-carboxylic acid are dissolved under nitrogen in 10 ml of tetrahydrofuran, and 58 mg (0.05 mmol) of tetrakis-(triphenylphosphine)-palladium (0) and 13 mg (0.05 mmol) of triphenylphosphine are added, and the mixture is stirred for 14 hours at room temperature. It is then filtered, the filtrate is freed from solvent under reduced pressure and the residue is crystallized from toluene. This gives 1.6 g (80% of theory) of racemic cis-1,3-dibenzyl-5-allyloxycarbonyl-2-oxoimidazolidine-4-carboxylic acid; $[\alpha]_{365}^{20} = 0.0°$ (c=1, dimethylformamide).

EXAMPLE 10

2 g (5.1 mmol) of (4S,5R)-cis-1,3-dibenzyl-5-allyloxycarbonyl-2-oxoimidazolidine-4-carboxylic acid are dissolved under nitrogen in 10 ml of tetrahydrofuran, and the solution is added dropwise to a solution of 0.05 mmol of tetrakis-(triphenylphosphine)-nickel (0) (obtained from nickel (II) acetylacetonate, triphenylphosphine and diisobutylaluminium hydride) in 5 ml of tetrahydrofuran. The mixture is stirred for 14 hours at room temperature and is then filtered, the filtrate is freed from solvent under reduced pressure and the residue is recrystallized from toluene. This gives 1.7 g (85% of theory) of cis-1,3-dibenzyl-5-allyloxycarbonyl-2-oxoimidazolidine-4-carboxylic acid; $[\alpha]_{365}^{20} = +0.4°$ (c=1, dimethylformamide).

EXAMPLE 11

12.0 g of (+)-ephedrinium (4R,5S)-cis-1,3-dibenzyl-5-allyloxycarbonyl-2-oxoimidazolidine-4-carboxylate in 500 ml of toluene to which 400 mg of tetrakis-(triphenylphosphine)-palladium (0) and 100 mg of triphenylphosphine have been added are heated at reflux temperature for 26 hours. The mixture is then stirred for 6 hours at 0° to 5°. The precipitated crystals of (+)-ephedrinium (4S,5S)-cis-1,3-dibenzyl-5-allyloxycarbonyl-2-oxoimidazolidine-4-carboxylate are removed (5.0 g; 83.3% of theory, relative to the enantiomer present), and 5.0 g of (4R,5S)-ephedrinium salt are added to the filtrate, at the boil. The rearrangement is complete after heating for 25 hours. 4.8 g (80.0% of theory) of (4S,5R)-ephedrinium salt crystallize at 5°. After this has been removed, a further 4.8 g of (4R,5S)-ephedrinium salt are added and rearrangement is carried out as indicated above, similarly good results being achieved.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for converting an enantiomer of an optically active dicarboxylic acid monoester into its antipode, said dicarboxylic acid monoester having the same skeletal structure as its opposite monoester, comprising subjecting the enantiomer to intramolecular rearrangement under transesterification conditions whereby its direction of rotation is reversed.

2. A process according to claim 1, wherein said intramolecular rearrangement is an intra-transesterification reaction.

3. A process according to claim 1, further comprising isolating said antipode by crystallization.

4. A process according to claim 2, further comprising isolating said antipode by crystallization.

5. A process according to claim 4, wherein crystallization of the antipode is performed during said transesterification reaction.

6. A process according to claim 2, wherein said transesterification reaction is performed in the presence of a catalyst, said catalyst being sulfuric acid, phosphoric acid, perchloric acid, methanesulfonic acid, toluenesulfonic acid or boric acid.

7. A process according to claim 5, wherein said transesterification reaction is performed in the presence of a catalyst, said catalyst being sulfuric acid, phosphoric acid, perchloric acid, methanesulfonic acid, toluenesulfonic acid or boric acid.

8. A process according to claim 1, wherein said antipode is converted to a diastereomeric salt by an opitcally active base and then isolated by chromatography, extractive distribution, mechanical selection or crystallization.

9. A process according to claim 2, wherein said transesterification reaction is performed in the presence of an inert solvent.

10. A process according to claim 5, wherein said transesterification reaction is performed in the presence of an inert solvent.

11. A process according to claim 6, wherein said transesterification reaction is performed in the presence of an inert solvent.

12. A process according to claim 7, wherein said transesterification reaction is performed in the presence of an inert solvent.

13. A process according to claim 10, wherein crystallization of said antipode is performed by converting the antipode to a diasteroemeric salt by means of an optically active base.

14. A process according to claim 13, wherein after crystallization, the isolated diastereomeric salt of the antipode is removed and additional enantiomer is added for conversion to its antipode.

15. A process according to claim 13, wherein after crystallization, the isolated diastereomeric salt of the antipode is removed and the corresponding diastereomeric salt of the enantiomer is added for conversion to its antipode.

16. A process according to claim 8, wherein said diastereomeric salt of the antipode is converted to the antipode by liberation with an acid.

17. A process according to claim 1, wherein said dicarboxylic acid monoester is a 1,3-dibenzyl-2-oxoimidazoline-4,5-dicarboxylic acid monoester.

18. A process according to claim 13, wherein said dicarboxylic acid monoester is a 1,3-dibenzyl-2-oxoimidazoline-4,5-dicarboxylic acid monoester.

19. A process for conversion of an enantiomer of an optically active dicarboxylic acid monoester into its racemic mixture, said dicarboxylic acid monoester having the same skeletal structure as its opposite monoester, comprising subjecting the enantiomer to intramolecular rearrangement under transesterification conditions whereby its direction of rotation is reversed.

20. A process according to claim 19, wherein said intramolecular rearrangement is an intra-transesterification reaction.

21. A process according to claim 20, further comprising converting the racemic mixture to a mixture of diastereomeric salts and crystallizing the diastereomeric salt of the antipode of said enantiomer.

22. A process according to claim 21, wherein said dicarboxylic acid monoester is a 1,3-dibenzyl-2-oxoimidazoline-4,5-dicarboxylic acid monoester.

* * * * *